United States Patent
Xiong et al.

(10) Patent No.: US 12,320,810 B2
(45) Date of Patent: Jun. 3, 2025

(54) CREATINE KINASE ISOENZYME ASSAY KIT

(71) Applicant: Beijing Strong Biotechnologies, Inc., Beijing (CN)

(72) Inventors: Zhengping Xiong, Beijing (CN); Wei Guo, Beijing (CN); Yao Liu, Beijing (CN); Xi Liu, Beijing (CN)

(73) Assignee: Beijing Strong Biotechnologies, Inc., Beijing (CN)

( * ) Notice: Subject to any disclaimer, the term of this patent is extended or adjusted under 35 U.S.C. 154(b) by 1131 days.

(21) Appl. No.: 16/982,664

(22) PCT Filed: Mar. 12, 2019

(86) PCT No.: PCT/CN2019/077813
§ 371 (c)(1),
(2) Date: Sep. 21, 2020

(87) PCT Pub. No.: WO2019/179333
PCT Pub. Date: Sep. 26, 2019

(65) Prior Publication Data
US 2021/0063397 A1 Mar. 4, 2021

(30) Foreign Application Priority Data
Mar. 22, 2018 (CN) .......................... 201810239106.5

(51) Int. Cl.
G01N 33/573 (2006.01)
C12Q 1/50 (2006.01)
G01N 33/543 (2006.01)

(52) U.S. Cl.
CPC ............. *G01N 33/573* (2013.01); *C12Q 1/50* (2013.01); *G01N 33/54306* (2013.01); *G01N 33/54313* (2013.01); *G01N 2333/9123* (2013.01)

(58) Field of Classification Search
CPC ........... G01N 33/573; G01N 33/54306; G01N 33/54313; G01N 2333/9123; C12Q 1/50
See application file for complete search history.

(56) References Cited

U.S. PATENT DOCUMENTS 4,267,271 A    5/1981   Roberts

FOREIGN PATENT DOCUMENTS

| CN | 103048464 A | 4/2013 |
|----|-------------|--------|
| CN | 103926405 A | 7/2014 |
| CN | 105334318 A | 2/2016 |
| CN | 106461662 A | 2/2017 |
| CN | 106645681 A | 5/2017 |
| CN | 106814193 A | 6/2017 |
| CN | 108548926 A | 9/2018 |
| EP | 1536236 A1  | 6/2005 |
| JP | 54119291 A  | 9/1979 |
| JP | 2013125005 A | 6/2013 |
| WO | 2015166790 A1 | 11/2015 |

OTHER PUBLICATIONS

Lewis Carl SA, Gillete-Ferguson I, Ferguson DG. An indirect immunofluorescence procedure for staining the same cryosection with two mouse monoclonal primary antibodies. Journal of Histochemistry & Cytochemistry. 1993;41(8): 1273-1278. doi: 10.1177/41.8.7687266 (Year: 1993).*
Written Opinion of the International Searching Authority; State Intellectual Property Office of the P.R. China; International Application No. PCT/CN2019/077813; Jun. 14, 2019; 9 pages.
International Search Report; State Intellectual Property Office of the P.R. China; International Application No. PCT/CN2019/077813; Jun. 14, 2019; 7 pages.

* cited by examiner

*Primary Examiner* — Louise W Humphrey
*Assistant Examiner* — John Paul Selwanes
(74) *Attorney, Agent, or Firm* — Taft Stettinius & Hollister LLP

(57) ABSTRACT

A creatine kinase isoenzyme latex-enhanced immunoturbidimetric assay kit, comprising a first reagent and a second reagent. The first reagent comprises a buffer solution, an electrolyte, polyethylene glycol, a surfactant, a preservative, a blocking agent, and a protective agent. The second reagent comprises a buffer solution, polystyrene latex particles coated with a creatine kinase isoenzyme antibody, the creatine kinase isoenzyme antibody on the latex particles, a protective agent, a stabilizer, and a preservative.

4 Claims, 1 Drawing Sheet

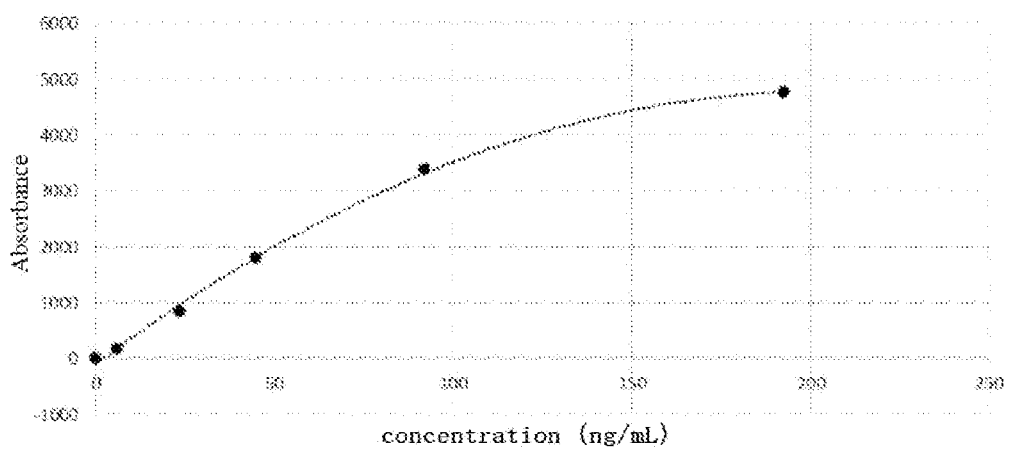

CREATINE KINASE ISOENZYME ASSAY KIT

CROSS-REFERENCE TO RELATED APPLICATIONS

This application is a U.S. National Phase of International PCT Application No. PCT/CN2019/077813 filed Mar. 12, 2019, which claims priority to Chinese Patent Application Serial No. 201810239106.5 filed Mar. 22, 2018, the contents of each application are incorporated herein by reference in their entirety.

FIELD OF THE INVENTION

The present application belongs to the field of in vitro diagnostics, and particularly relates to the detection of creatine kinase (CK) isoenzyme by immunoturbidimetry.

BACKGROUND OF THE INVENTION

CK was first studied and considered to be useful for the diagnosis of ACS in 1960. However, it was replaced by creatine kinase isoenzyme (CKMB) after 1970 due to its poor specificity. Subsequently, CKMB was recommended as the previous generation gold standard for the diagnosis of myocardial infarction (AMI) due to its better specificity and sensitivity.

However, trace amount of CKMB is also present in skeletal muscles, and the amount of CKMB present in skeletal muscles in children is even higher. Therefore, the specificity is not satisfying and there is a risk of misdiagnosis. Currently, it has been replaced by novel gold standard marker, cTnI.

Even so, CKMB still has important clinical implication in the diagnosis of ACS and AMI. Firstly, when myocardial damage triggers the onset of chest pain, CKMB appears in blood earlier than cTnI, so it can be used as a marker for early diagnosis. Secondly, CKMB is a preferred marker for evaluation of the effect of thrombolytic therapy. When the occluded myocardial coronary artery is recanalized, CKMB in the cardiomyocytes will be washed out along with the blood, causing the increase of CKMB. Based on such feature, the effect of thrombolytic therapy may be evaluated based on the change of the concentration of CKMB. Thirdly, myocardial infarct area and reinfarction may be assessed by detecting CKMB. Finally, in case that cTnI is not available or a definite diagnosis cannot be made from the results of cTnI, CKMB is an effective auxiliary marker for cTnI.

At present, immunosuppression assay, which measures the activity of CK-MB, is mainly utilized as conventional detection method for CK-MB. There is little CK-BB in normal human body, thus, the presence of CK-BB can be negligible during such assay, and it is assumed that only CK-MM and CK-MB are present in serum. Polyclonal antibody against CK-M subunit is added into the reagent to inhibit the activity of M subunit in CK-MM and CK-MB, and the result of the assay corresponds to the activity of B subunit in CK-MB, which is multiplied by 2 to obtain the activity of CK-MB. This assay is quick, concise, time-saving, and highly sensitive, but also suffers from many influence factors and defects.

Enzyme-linked immunosorbent assay (ELISA) is to detect the presence of CK-MB in serum based on sandwich assay using two antibodies. The main principle is in that, a 96-well plate is coated with one of the paired monoclonal antibodies, the serum sample to be tested is added into the well of plate, incubated for a period of time, the plate is washed to remove the excess liquid, and the other monoclonal antibody carrying HRP tag is the added, and finally developed in the presence of TMB. The concentration of CK-MB in the sample is determined based on the absorbance. This assay is highly specific, but requires manual operation and long time period for detection.

As for colloidal gold immunoturbidimetry, for example, a kit for detecting creatine kinase isoenzyme disclosed in CN103926405A comprises a first reagent and a second reagent, wherein the first reagent comprises: 0.2% BSA, 0.05% TWEEN® 20, 50 mM phosphate buffer pH 7.2, 0.2% PEG 20000, and 0.1% $NaN_3$; and the second reagent comprises: 1% BSA, 50 nm to 100 nm gold particle, 10 mmol phosphate buffer pH 7.2, 0.1% $NaN_3$, 20% sucrose, and 5% glycerol.

Electrochemiluminescence (ECL) is a specific chemiluminescence reaction initiated by electrochemistry on the surface of the electrode. The advantages of this method involve strong specificity and excellent precision, and the disadvantages are high cost and mainly owned by IVD giants.

Rheumatoid factor (RF) present in patients will interfere with many immunological assays. IgM Type and IgG Type of RF bind to Fc of both capture antibody and labeled secondary antibody in the detection reagent, resulting in false positive result. RF interferes with various detection methods at different degrees, which are not proportional to RF concentrations. At present, most of the detection reagents used in the clinic do not take enough measures to avoid RF interference (Research Progress on Interference of Rheumatoid Factor on Immunoassay, Medical Review 2015 Vol 21, 19:3495). At present, the strategies to avoid RF interference include: pretreating the samples to be tested with solid phase adsorbent agent conjugated to heat-denatured IgG (Euroimmune) at 4° C. overnight, and centrifuging for detection assay; adding 2-mercaptoethanol into the sample dilutions or into the samples when detecting the antigen, so that Type IgM of RF can be dissociated.

In view of the above, there is still a need in the art for a kit for detecting CKMB with high specificity, low false positivity, resistance to RF interference, and low cost.

SUMMARY OF THE INVENTION

According to some embodiments, provided is a kit for detecting creatine kinase isoenzyme by latex-enhanced immunoturbidimetry, comprising a first reagent and a second reagent, wherein the first reagent comprises:

| | |
|---|---|
| 10 mM-100 mM | buffer, |
| 5 g/L-50 g/L | electrolyte, |
| 1 g/L-10 g/L | polyethylene glycol, |
| 1 g/L-20 g/L | surfactant, |
| 0.5 g/L-1.5 g/L | preservative, |
| 0.1%-2%, v/v | blocking agent, |
| 1 g/L-20 g/L | protective agent, |
| | pH 6.5-8.5; | the second reagent comprises:

| | |
|---|---|
| 10 mM-100 mM | buffer, |
| 0.1%-0.5%, w/v | polystyrene latex particle coated with antibody against creatine kinase isoenzyme, |
| 0.02 g/L-0.05 g/L | antibody against creatine kinase isoenzyme on said latex particle, |

| 1 g/L-20 g/L | protective agent, |
| 20 g/L-200 g/L | stabilizer, |
| 0.5 g/L-1.5 g/L | preservative, |
| | pH 6.5-8.5. |

In some embodiments, the buffer is selected from the group consisting of glycine buffer, TRIS™-HCl buffer and HEPES buffer.

In some embodiments, the preservative is selected from the group consisting of sodium azide, thimerosal and PRO-CLIN® 300.

In some embodiments, the polyethylene glycol is selected from the group consisting of PEG 6000, PEG 8000, PEG 12000 and PEG 20000, preferably is PEG 20000.

In some embodiments, the surfactant is selected from the group consisting of TWEEN® 20, TWEEN® 80, NP-40™ and THESIT®.

In some embodiments, the surfactant is TWEEN® 80.

In some embodiments, the protective agent is selected from the group consisting of bovine serum albumin, ovalbumin, skim milk and calf serum.

In some embodiments, the blocking agent is goat anti-mouse IgG. Without being particularly limited to theory, Rheumatoid Factor (RF) present in patients will interfere with many immunological assays. IgM Type and IgG Type of RF bind to Fc of both the capture antibody and the labeled secondary antibody in the detection reagent, resulting in false positive result. The inventors have unexpectedly discovered that goat anti-mouse IgG (not associated with specific sequence of the antibody) is effective in masking the RF present in the patients and alleviates the false positive result.

In some embodiments, the stabilizer is selected from the group consisting of sucrose, glycerol, trehalose and glucose.

In some embodiments, the stabilizer is sucrose.

In some embodiments, the surface functional group of the polystyrene latex particle is selected from the group consisting of amino group, carboxyl group, chloromethyl group and epoxy group, preferably is carboxyl group.

In some embodiments, the polystyrene latex particle has an average particle size of from 200 nm to 500 nm, preferably 300 nm. The skilled person will understand that, for example, "the particle size of the polystyrene latex particle is 300 nm", it does not mean that the particle size of each of the latex particles present in the reagent is strictly 300 nm. In fact, it is impossible to achieve completely uniform particle size of each latex particle during the preparation of commercial latex particles. Latex particle (Type 300 nm) means that the particle sizes of the latex particles are normally distributed around 300 nm (for example, but not limited to, within ±20%). Therefore, the particle size may be understood as the average particle size of the latex particles.

In some embodiments, the antibody against creatine kinase isozyme is derived from mouse or goat.

In some embodiments, the antibody against creatine kinase isozyme is monoclonal antibody.

According to some embodiments, provided is a kit for detecting creatine kinase isoenzyme by latex-enhanced immunoturbidimetry, comprising a first reagent and a second reagent, wherein the first reagent comprises:

| 50 mM | HEPES buffer, |
| 8.77 g/L | NaCl, |
| 9 g/L | PEG20000, |
| 10 g/L | Tween 80, |
| 1.0 g/L | sodium azide, |
| 1%, v/v | blocking agent, |
| 5 g/L | BSA, |
| | pH 7.2; | the second reagent comprises:

| 50 mM | glycine buffer, |
| 0.1%-0.5%, w/v | polystyrene latex particle coated with antibody against creatine kinase isoenzyme, |
| 0.02 g/L-0.05 g/L | antibody against creatine kinase isoenzyme on said latex particle, |
| 5 g/L | BSA, |
| 1 g/L | sodium azide, |
| 100 g/L | sucrose, |
| | pH 7,5; | the antibody is murine monoclonal antibody;

the average particle size of the latex particles is 300 nm;

the latex particle is modified with carboxyl group; and the blocking agent is goat anti-mouse IgG.

According to some embodiments, provided is a kit for detecting creatine kinase isoenzyme by latex-enhanced immunoturbidimetry, comprising a first reagent and a second reagent, wherein the first reagent comprises:

| 50 mM | HEPES buffer, |
| 8.77 g/L | NaCl, |
| 9 g/L | PEG20000, |
| 10 g/L | Tween 20, |
| 1.0 g/L | sodium azide, |
| 1%, v/v | blocking agent, |
| 5 g/L | BSA, |
| | pH 7.2; | the second reagent comprises:

| 50 mM | glycine buffer, |
| 0.1%-0.5%, w/v | polystyrene latex particle coated with antibody against creatine kinase isoenzyme, |
| 0.02 g/L-0.05 g/L | antibody against creatine kinase isoenzyme on said latex particle, |
| 5 g/L | BSA, |
| 1 g/L | sodium azide, |
| 100 g/L | sucrose, |
| | pH 7.5; | the antibody is murine monoclonal antibody;

the average particle size of the latex particles is 300 nm;

the latex particle is modified with carboxyl group; and the blocking agent is goat anti-mouse IgG.

According to some embodiments, provided is a kit for detecting creatine kinase isoenzyme by latex-enhanced immunoturbidimetry, comprising a first reagent and a second reagent, wherein the first reagent comprises:

| 50 mM | glycine buffer, |
| 8.77 g/L | NaCl, |
| 9 g/L | PEG20000, |
| 10 g/L | Tween 80, |

-continued

| | |
|---|---|
| 1.0 g/L | sodium azide, |
| 1%, v/v | blocking agent, |
| 5 g/L | BSA, |
| | pH 7.2; | the second reagent comprises:

| | |
|---|---|
| 50 mM | Tris buffer, |
| 0.1%-0.5%, w/v | polystyrene latex particle coated with antibody against creatine kinase isoenzyme, |
| 0.02 g/L-0.05 g/L | antibody against creatine kinase isoenzyme on said latex particle, |
| 5 g/L | BSA, |
| 1 g/L | sodium azide, |
| 100 g/L | sucrose, |
| | pH 7.5; | the antibody is murine monoclonal antibody;
the average particle size of the latex particles is 300 nm;
the latex particle is modified with carboxyl group; and
the blocking agent is goat anti-mouse IgG.

According to some embodiments, provided is a blocking agent, for use in improving false positive detection result.

In some embodiments, the blocking agent is goat anti-mouse IgG. In some embodiments, the detection is an assay for creatine kinase isoenzyme by latex-enhanced immunoturbidimetry.

According to some embodiments, provided is use of a blocking agent to improve detection from RF interference. In some embodiments, the blocking agent is goat anti-mouse IgG. In some embodiments, the detection refers to an assay for creatine kinase isoenzyme based on latex-enhanced immunoturbidimetry.

In some embodiments, the detection is improved in the aspects of RF interference and false positive detection result, by incorporating the blocking agent into the detection reagent at 0.1% to 2%, v/v.

DESCRIPTION OF THE DRAWINGS

The FIGURE shows the calibration curve obtained by using the kit of the present application.

DETAILED DESCRIPTION OF THE DISCLOSURE

Example 1. Preparation of the First Reagent 1. 17.87 g HEPES, 13.15 g NaCl, 9 g PEG20000, 15 g TWEEN® 80, 1.5 g sodium azide, 7.5 g BSA and 15 mL blocking agent (5 mg/ml) were weighed and dissolved in 1.0 L double distilled water, pH was adjusted to 7.2, and the total volume was adjusted to 1.5 L to obtain the first reagent (1):

| | |
|---|---|
| 50 mM | HEPES buffer, |
| 8.77 g/L | NaCl, |
| 9 g/L | PEG20000, |
| 10 g/L | Tween 80, |
| 1.0 g/L | sodium azide, |
| 1%, v/v | blocking agent, |
| 5 g/L | BSA, |
| | pH 7.2. |

2. Alternatively, 9.09 g TRIS™, 13.15 g NaCl, 9 g PEG 20000, 15 g TWEEN® 80, 1.5 g sodium azide, 7.5 g BSA and 10 mL blocking agent (the same as mentioned above) were weighed and dissolved in 1.0 L double distilled water, pH was adjusted to 7.2, and the total volume was adjusted to 1.5 L to obtain the first reagent (2):

| | |
|---|---|
| 50 mM | Tris buffer, |
| 8.77 g/L | NaCl, |
| 9 g/L | PEG20000, |
| 10 g/L | Tween 80, |
| 1.0 g/L | sodium azide, |
| 1%, v/v | blocking agent, |
| 5 g/L | BSA, |
| | pH 7.2. |

3. Alternatively, 5.63 g glycine, 13.15 g NaCl, 9 g PEG20000, 15 g TWEEN®80, 1.5 g sodium azide, 7.5 g BSA, 10 mL blocking agent (the same as above) were weighed and dissolved in 1.0 L double distilled water, pH was adjusted to 7.2, and the total volume was adjusted to 1.5 L to obtain the first reagent (3):

| | |
|---|---|
| 50 mM | glycine buffer, |
| 8.77 g/L | NaCl, |
| 9 g/L | PEG20000, |
| 10 g/L | Tween 80, |
| 1.0 g/L | sodium azide, |
| 1%, v/v | blocking agent, |
| 5 g/L | BSA, |
| | pH 7.2. |

Example 2. Preparation of Particles Coated with Antibody

1. The particles (300 nm, carboxyl group) were diluted to 1% (w/v) with HEPES buffer;
2. The antibody (mouse monoclonal antibody) was diluted to 0.5 mg/ml with HEPES buffer;
3. The particles obtained from step 1 were added with 0.1% to 1% (w/v) of EDAC aqueous solution, and incubated at 37° C. for 30 min in a shaker at constant temperature;
4. After the reaction was completed, the antibody obtained from step 2 was added, and reacted at 37° C. for 3 h in a constant temperature shaker;
5. Then a blocking agent was added and incubated at room temperature overnight;
6. The particles which have been blocked overnight were washed and centrifuged for 3 times with washing solution and then stored for use.

Steps 1 and 2 may be interchangeable.

Example 3. Preparation of the Second Reagent

1. The particles prepared in Example 2 were added into 400 mL double distilled water, supplemented with 18.76 g glycine, 2.5 g BSA, 0.5 g sodium azide, 50 g sucrose, stirred and mixed, pH was adjusted to 7.5, supplemented with double distilled water to 500 mL, and ultrasonicated until the absorbance at the main wavelength was substantially stable. The second reagent (1) was obtained:

| | |
|---|---|
| 50 mM | glycine buffer, |
| 0.1%-0.5%, w/v | polystyrene latex particle coated with antibody, |
| 0.02 g/L-0.05 g/L | antibody on the latex particle, |
| 5 g/L | BSA, |
| 1 g/L | sodium azide, |
| 100 g/L | sucrose, |
| | pH 7.5. |

2. Alternatively, the particles prepared in Example 2 were added into 400 mL double distilled water, supplemented with 5.96 g HEPES, 2.5 g BSA, 0.5 g sodium azide, 50 g sucrose, stirred and mixed, pH was adjusted to 7.5, supplemented with double distilled water to 500 mL, and ultrasonicated until the absorbance at the main wavelength was substantially stable. The second reagent (2) was obtained:

| | |
|---|---|
| 50 mM | HEPES buffer, |
| 0.1%-0.5%, w/v | polystyrene latex particle coated with antibody, |
| 0.02 g/L-0.05 g/L | antibody on the latex particle, |
| 5 g/L | BSA, |
| 1 g/L | sodium azide, |
| 100 g/L | sucrose, |
| | pH 7.5. |

3. Alternatively, the particles prepared in Example 2 were added into 400 mL double distilled water, supplemented with 3.03 g TRIS™, 2.5 g BSA, 0.5 g sodium azide, 50 g sucrose, stirred and mixed, pH was adjusted to 7.5, supplemented with double distilled water to 500 mL, and ultrasonicated until the absorbance at the main wavelength was substantially stable. The second reagent (3) was obtained:

| | |
|---|---|
| 50 mM | Tris buffer, |
| 0.1%-0.5%, w/v | polystyrene latex particle coated with antibody, |
| 0.02 g/L-0.05 g/L | antibody on the latex particle, |
| 5 g/L | BSA, |
| 1 g/L | sodium azide, |
| 100 g/L | sucrose, |
| | pH 7.5. |

Example 4. Preparation of the Kit

The kits were assembled with the reagents mentioned above according to the following table.

TABLE 1

Assembly of the kit

| | the first reagent | the second reagent |
|---|---|---|
| Kit 1 | the first reagent (1) | the second reagent (1) |
| Kit 2 | the first reagent (2) | the second reagent (1) |
| Kit 3 | the first reagent (3) | the second reagent (1) |
| Kit 4 | the first reagent (2) | the second reagent (2) |
| Kit 5 | the first reagent (3) | the second reagent (2) |
| Kit 6 | the first reagent (3) | the second reagent (3) |

Test Examples

Test Example 1. Test for Sensitivity

The six kits prepared in the above examples were tested using an automatic biochemical analyzer (for example, Hitachi 7180).

The measurement wavelength was at 660 nm, and the sampling amount was 10 μL. 150 μL of the first reagent was added, incubated at constant temperature of 37° C. for 5 min, then 50 μL of the second reagent was added, the absorbance A1 was read 42 seconds later, and the absorbance A2 was read after incubating at 37° C. for 4 minutes and 18 seconds. The reaction absorbance was calculated as $\Delta A = A2 - A1$. The performance of the above six examples was tested, and the results are shown as follows:

TABLE 2

Results of detection limit

| | No. of Kit | | | | | |
|---|---|---|---|---|---|---|
| Performance | 1 | 2 | 3 | 4 | 5 | 6 |
| Detection limit (ng/ml) | 1.10 | 1.32 | 1.56 | 1.78 | 1.65 | 1.35 |
| Precision (%) Low-value quality control | 2.54 | 3.58 | 2.95 | 2.65 | 3.78 | 3.15 |

According to the above measurement, it was found that all the kits 1 to 6 achieved good sensitivity, among which kit 1 was optimal with sensitivity of 1 ng/ml.

Test Example 2. The Selection of Surfactant

The following kits were prepared according to the preparation method for Kit 1, except that the surfactant TWEEN® 80 was replaced with TWEEN® 20, NP-40™ and THESIT®, respectively, and the anti-interference effect against the triglyceride was tested.

TABLE 3

Screening of surfactant

| | surfactant | | | |
|---|---|---|---|---|
| | Tween 80 | Tween 20 | NP40 | thesit |
| Control (without interference) | 7.44 | 7.47 | 6.84 | 7.04 |
| 1000 mg/dL triglyceride | 7.49 | 7.68 | 8.01 | 7.65 |
| Relative deviation | 0.67% | 2.81% | 17.11% | 8.66% |

Test Example 3. Effect of Blocking Agent on False Positive Results

The comparative kit was prepared according to the preparation method of Kit 1, except that the blocking agent was absent. Samples with or without 500 IU/ml RF were tested with each kit prepared. The results are shown as follows, showing that the blocking agent can significantly improve the detection results from being false positive and can avoid RF interference.

TABLE 4

Effect of blocking agent on false positive results

| blocking agent | Blank control without RF | with RF (500 IU/ml) | Recovery rate |
|---|---|---|---|
| Without blocking agent | 47.20 ng/ml | 200.2 ng/ml | 424% |
| With blocking agent | 47.45 ng/ml | 48.23 ng/ml | 101.6% |

What is claimed is:

1. A kit for detecting creatine kinase isoenzyme by latex-enhanced immunoturbidimetry, comprising a first reagent and a second reagent, wherein the first reagent comprises:

| | |
|---|---|
| 10 mM-100 mM | buffer, |
| 5 g/L-50 g/L | electrolyte, |
| 1 g/L-10 g/L | polyethylene glycol, |
| 1 g/L-20 g/L | surfactant, |
| 0.5 g/L-1.5 g/L | preservative, |
| 0.1%-2%, v/v | blocking agent, |
| 1 g/L-20 g/L | protective agent, |
| | pH 6.5-8.51; | the second reagent comprises:

| | |
|---|---|
| 10 mM-100 mM | buffer, |
| 0.1%-0.5%, w/v | polystyrene latex particle coated with antibody against creatine kinase isoenzyme, |
| 0.02 g/L-0.05 g/L | antibody against creatine kinase isoenzyme on said latex particle, |
| 1 g/L-20 g/L | protective agent, |
| 20 g/L-200 g/L | stabilizer, |
| 0.5 g/L-1.5 g/L | preservative, |
| | pH 6.5-8.51; | the buffer in the first reagent is selected from the group consisting of glycine buffer and HEPES buffer;

the buffer in the second reagent is selected from the group consisting of glycine buffer, and 2-amino-2-(hydroxymethyl)-1,3-propanediol HCl buffer;

the preservative in the first reagent and in the second reagent is selected from the group consisting of sodium azide, thimerosal and a mixture of 5-chloro-2-methyl-4-isothiazolin-3-one and 2-methyl-4-isothiazoin-3-one;

the polyethylene glycol is selected from the group consisting of PEG 6000, PEG 8000, PEG 12000 and PEG 20000;

the surfactant is selected from the group consisting of polysorbate 20, polysorbate 80, octylphenoxy polyethoxyethanol and polyethylene glycol dodecyl ether;

the protective agent in the first reagent and in the second reagent is selected from the group consisting of bovine serum albumin, ovalbumin, skim milk and calf serum;

the blocking agent is goat anti-mouse IgG;

the stabilizer is selected from the group consisting of sucrose, glycerol, trehalose and glucose;

the polystyrene latex particle is modified with carboxyl group;

the polystyrene latex particle has an average particle size of from 200 nm to 500 nm;

the antibody against creatine kinase isozyme is derived from mouse or goat; and the antibody against creatine kinase isozyme is monoclonal antibody.

2. The kit for detecting creatine kinase isoenzyme by latex-enhanced immunoturbidimetry according to claim 1, comprising a first reagent and a second reagent, wherein the first reagent comprises:

| | |
|---|---|
| 50 mM | HEPES buffer, |
| 8.77 g/L | NaCl, |
| 9 g/L | PEG20000, |
| 10 g/L | Tween 80, |
| 1.0 g/L | sodium azide, |
| 1%, v/v | blocking agent, |
| 5 g/L | BSA, |
| | pH 7.2; | the second reagent comprises:

| | |
|---|---|
| 50 mM | glycine buffer, |
| 0.1%-0.5%, w/v | polystyrene latex particle coated with antibody against creatine kinase isoenzyme, |
| 0.02 g/L-0.05 g/L | antibody against creatine kinase isoenzyme on the latex particle, |
| 5 g/L | BSA, |
| 1 g/L | sodium azide, |
| 100 g/L | sucrose, |
| | pH 7.5; | the antibody is murine monoclonal antibody;

the average particle size of the latex particles is 300 nm;

the latex particle is modified with carboxyl group; and the blocking agent is goat anti-mouse IgG.

3. The kit for detecting creatine kinase isoenzyme by latex-enhanced immunoturbidimetry according to claim 1, comprising a first reagent and a second reagent, wherein the first reagent comprises:

| | |
|---|---|
| 50 mM | HEPES buffer, |
| 8.77 g/L | NaCl, |
| 9 g/L | PEG20000, |
| 10 g/L | Tween 20, |
| 1.0 g/L | sodium azide, |
| 1%, v/v | blocking agent, |
| 5 g/L | BSA, |
| | pH 7.2; | the second reagent comprises:

| | |
|---|---|
| 50 mM | glycine buffer, |
| 0.1%-0.5%, w/v | polystyrene latex particle coated with antibody against creatine kinase isoenzyme, |
| 0.02 g/L-0.05 g/L | antibody against creatine kinase isoenzyme on the latex particle, |
| 5 g/L | BSA, |
| 1 g/L | sodium azide, |
| 100 g/L | sucrose, |
| | pH 7.5; | the antibody is murine monoclonal antibody;

the average particle size of the latex particles is 300 nm;

the latex particle is modified with carboxyl group; and the blocking agent is goat anti-mouse IgG.

4. The kit for detecting creatine kinase isoenzyme by latex-enhanced immunoturbidimetry according to claim 1, comprising a first reagent and a second reagent, wherein the first reagent comprises:

| | |
|---|---|
| 50 mM | glycine buffer, |
| 8.77 g/L | NaCl, |
| 9 g/L | PEG20000, |
| 10 g/L | Tween 80, |
| 1.0 g/L | sodium azide, |
| 1%, v/v | blocking agent, |
| 5 g/L | BSA, |
| | pH 7.2; | the second reagent comprises:

| | |
|---|---|
| 50 mM | Tris buffer, |
| 0.1%-0.5%, w/v | polystyrene latex particle coated with antibody against creatine kinase isoenzyme, |
| 0.02 g/L-0.05 g/L | antibody against creatine kinase isoenzyme on the latex particle, |
| 5 g/L | BSA, |
| 1 g/L | sodium azide, |
| 100 g/L | sucrose, |
| | pH 7.5; | the antibody is murine monoclonal antibody;
the average particle size of the latex particles is 300 nm;
the latex particle is modified with carboxyl group; and
the blocking agent is goat anti-mouse IgG.

* * * * *

UNITED STATES PATENT AND TRADEMARK OFFICE
CERTIFICATE OF CORRECTION

PATENT NO. : 12,320,810 B2
APPLICATION NO. : 16/982664
DATED : June 3, 2025
INVENTOR(S) : Zhengping Xiong et al.

Page 1 of 1

It is certified that error appears in the above-identified patent and that said Letters Patent is hereby corrected as shown below:

In the Claims

Claim 1 at Column 9, Lines 14 and 25:
1. Delete "pH 6.5-8.51" and insert --pH 6.5-8.5--.

Claim 1 at Column 9, Line 22:
2. Delete "said" and insert --the--.

(i) Claim 2 at Column 9, Line 66, (ii) Claim 3 at Column 10, Line 32, and (iii) Claim 4 at Column 10, Line 62:
3. Delete "Tween" and insert --polysorbate--.

Claim 4 at Column 11, Line 3:
4. Delete "Tris" and insert --2-amino-2-(hydroxymethyl)-1,3-propanediol HCl--.

Signed and Sealed this
Fifteenth Day of July, 2025

Coke Morgan Stewart
*Acting Director of the United States Patent and Trademark Office*